(12) United States Patent
Schmid et al.

(10) Patent No.: US 6,991,926 B2
(45) Date of Patent: Jan. 31, 2006

(54) METHOD COMPRISING THE INDIRECT ELECTROCHEMICAL REGENERATION OF NAD(P)H

(75) Inventors: Andreas Schmid, Zürich (CH); Frank Hollmann, Zürich (CH); Bernhard Hauer, Fussgönheim (DE); Thomas Zelinski, Altrip (DE); Eberhard Steckhan, deceased, late of Meckenheim (DE); by Christiane Karla Steckhan, legal representative, Meckenheim (DE); by Uwe Steckhan, legal representative, Meckenheim (DE); by Antje Steckhan, legal representative, Meckenheim (DE); by Heike Steckhan, legal representative, Meckenheim (DE)

(73) Assignee: Basf Aktiengesellschaft, Ludwigshafen (DE)

( * ) Notice: Subject to any disclaimer, the term of this patent is extended or adjusted under 35 U.S.C. 154(b) by 407 days.

(21) Appl. No.: 10/276,227

(22) PCT Filed: May 16, 2001

(86) PCT No.: PCT/EP01/05601

§ 371 (c)(1),
(2), (4) Date: Nov. 14, 2002

(87) PCT Pub. No.: WO01/88172

PCT Pub. Date: Nov. 22, 2001

(65) Prior Publication Data

US 2003/0162270 A1    Aug. 28, 2003

(30) Foreign Application Priority Data

May 17, 2000    (DE)    ............................... 100 24 314

(51) Int. Cl.
*C12P 13/00*     (2006.01)
*C12P 7/22*      (2006.01)
*C12N 13/00*     (2006.01)
*C12M 1/00*      (2006.01)

(52) U.S. Cl. .................... 435/128; 435/156; 435/173.2; 435/289.1; 435/299.1

(58) Field of Classification Search ................ 435/128, 435/156, 173.2, 289.1, 299.1
See application file for complete search history.

(56) References Cited

U.S. PATENT DOCUMENTS 6,599,722 B2 *    7/2003    Boston et al. .............. 435/137

OTHER PUBLICATIONS a) Hummel,W., et al., *Eur. J. Biochem.* 1989, 184, 1-13; b) Shaked, Z., et al., *J. Am. Chem. Soc.* 1980, 102, 7104-7108; c) Abril, O., et al., *Bioorg. Chem.* 1989, 17, 41-52; d) Seelbach, K., et al., *Tetrahedron Lett.* 1996, 37, 1377-1380.
a) Hilt, G., et al., *Liebigs Ann./Recueil* 1997, 2289-2296; b) Westerhausen, D., et al., *Angew. Chem.* 1992, 104, 1496-1498; *Angew. Chem. Int. Ed. Engl.* 1992, 31, 1529-1531 c) Ruppert, R., et al *Tetrahedron Lett.* 1987, 52(28), 6583-6586.
a) Walsh, C.T.*Acc. Chem. Res.* 1980, 13, 148-155; b) Walsh, C.T. et al., *Angew. Chem.* 1988, 100, 342-352; *Angew. Chem. Int. Ed. Engl.* 1988.
Wong, C.-H., et al., *J. Am. Chem. Soc.* 1981, 103, 4890-4899.
a) Hummel, W., et al.; *Appl. Microbiol Biotechnol.* 1986, 25, 175-185; b) Rissom, R., et al., *Tetrahedron Asymmetry* 1997, 15(8), 2523-2526.
Suske,W. A., et al., *J. Biol. Chem.*, 1997, 272 (39), 24257-242565.
Held, M., et al., *Biotechnol. Bioeng.*, 1999, 62 (6), 641-648.
Wandrey, C., *Chem. Ing. Tech.* 1976, 48, 537.
Reipa, V., et al., *Proc.Natl. Acad. Sci.* USA, 1997, 94, 13554-13558.
Brielbeck, B., et al., Biocatalysis, 1994, 10, 49.
Schneider et al., *Enzyme Microbiol. Technol.*, 1995, 17, 839.
a) Steckhan, E., et al., *Organometallics*, 1991, 10, 1568-1577; b) Ruppert, R., et al.,*J. Chem. Soc., Chem. Commun.*, 1988, 1150-1151.
Kölle, U., et al., *Angew. Chem.* 1987, 99, 572.
Kölle, U., et al., *Chem.Ber.* 1989, 122, 1869.
Kragl, U., et al., Chem. Ing. Tech., 1992, 499.
H. Fretz, W. D. Woggon, R. Voges *Hel. Chim. Acta* , 1989., 72, 391-400.
H. L. Holland, T. S. Manoharan, F. Schweizer *Tetrahedron: Asymmetry*, 1991, 2, 335-338.
S. W. May, B. J. Abbot *J. Biol. Chem.* 1973 ,248 , 1725-1730.
Roberts et al. *J. Mol. Cat. B Enzymatic*, 1998 , 4, 111 ff.

* cited by examiner

*Primary Examiner*—Herbert J. Lilling
(74) *Attorney, Agent, or Firm*—Novak Druce & Quigg LLP (57) ABSTRACT

A method comprising the indirect electrochemical regeneration of NAD(P)H in enzymatic substrate conversions which are catalyzed by monooxygenases, for example, is described. In particular, a method for the electroenzymatic preparation of 2,3-dihydroxyphenyl derivatives, which is catalyzed by the enzyme 2-hydroxybiphenyl 3-monooxygenase and in which simultaneously the $NAD^+$ formed by reductive cleavage of oxygen is electrochemically reduced, is described.

15 Claims, 6 Drawing Sheets

METHOD COMPRISING THE INDIRECT ELECTROCHEMICAL REGENERATION OF NAD(P)H

The present invention relates to a method comprising the indirect electrochemical regeneration of NAD(P)H from NAD(P)⁺ which is generated, for example, in the enzyme-catalyzed reductive cleavage of oxygen. The electrochemical regeneration method of the invention is in particular applicable within the scope of electroenzymatic, NAD(P)H-consuming conversions, in particular of oxidative enzymatic conversions of substrates by monooxygenases. The invention relates in particular to an electroenzymatic method for the monooxygenase-catalyzed preparation of 2,3-dihydroxyphenyl derivatives.

Biocatalyzed reactions are gaining more and more importance both in organic synthesis in the laboratory and in numerous industrial applications. In particular, the usually high regio- and stereoselectivities of enzymatic conversions with, at the same time, mild conditions and high yields make them attractive tools in synthesis planning. In contrast to the hydrolytic enzymes which are already used in many different ways, the use of redox enzymes for enantioselective reductions and chemo-, regio- and enantioselective oxidations is not very widespread yet, despite their great potential for synthesis. The reason for this is especially the problem of an effective cofactor regeneration, which has not been solved satisfactorily up until now. Besides the established methods of enzyme-coupled cofactor regeneration [1a,b,c,d], electrochemical methods have now been developed and applied to NAD(P)⁺- and NAD(P)H-dependent enzymes [2a,b,c]. The advantage of the indirect electrochemical cofactor regeneration is that merely the producer enzyme is required and thus the often difficult optimization of a double-enzyme system is unnecessary. Moreover, a cosubstrate can be dispensed with.

Monooxygenases are of great importance in synthesis, since they are able to incorporate oxygen functions regio- and stereoselectively into their substrates. In order to do this, they require molecular oxygen whose O—O bond is reductively cleaved with the formation of water [3a,b]. The native cofactors of monooxygenases, NADH or NADPH, deliver the necessary reduction equivalents for this purpose. The previous in vitro methods with monooxygenases as producer enzymes are based on an enzyme-coupled cofactor regeneration using formate dehydrogenase [4a,b] (for NADH or NADPH) and glucose-6-phosphate dehydrogenase [5] (for NADPH).

Reipa et al. [10] describe a method for the electrochemical regeneration of putidaredoxin, the natural redox partner of cytochrome CYP 101 monooxygenase (E.C.1.14.15.1). For said method it is suggested to use a special antimony-doped tin oxide electrode which is suitable for putidaredoxin reduction.

Held et al. [8] describe the biocatalytic production of 3-phenylcatechol using whole cells of *Escherichia coli* JM 101 (PHDT 461). Said recombinant microorganism has been designed for producing the enzyme 2-hydroxybiphenyl 3-monooxygenase. In this connection, electrochemical regeneration of NADH consumed is not required, since the enzymatic system of the intact *E. coli* cells regenerates the cofactor.

It is an object of the present invention to develop an enzyme-free, selective and effective method for indirect electrochemical NAD(P)H regeneration, which is suitable, for example coupled to monooxygenases, for the oxidative conversion of substrates with reductive cleavage of oxygen.

Another object is to provide a method which facilitates the enzymatic, monooxygenase-catalyzed synthesis of 2,3-dihydroxyphenyl compounds, such as 2,3-dihydroxybiphenyl, with indirect electrochemical NAD(P)H regeneration.

We have found that this object is achieved by providing an electroenzymatic method for preparing 2,3-dihydroxyphenyl derivatives of the formula I where R is unsubstituted, monosubstituted or polysubstituted phenyl, $C_1$–$C_6$ alkyl, halogen or CN; and R' is H or OH;

which method comprises a) converting a monohydroxyphenyl compound of the formula II where R and R' have the abovementioned meanings, using 2-hydroxybiphenyl 3-monooxygenase (HbpA) (E.C.1.14.13.44) in the presence of NADH and oxygen; and b) reducing the NAD⁺ formed to NADH electrochemically.

The objects are also achieved by providing a method for NAD(P)H regeneration in an NAD(P)H-consuming oxidative enzymatic conversion of a substrate, which method comprises carrying out an NAD(P)H-consuming oxidative enzymatic conversion of an oxidizable substrate in the presence of. NAD(P)H and preferably with oxygen consumption and reducing the NAD(P)⁺ formed in the course of substrate oxidation electrochemically to give NAD(P)H. It is possible, for example, to incubate an NAD(P)H-dependent monooxygenase (from the class E.C. 1.14.-.-) with the oxidizable substrate in the presence of NAD(P)H and oxygen and to reduce electrochemically the NAD(P)⁺ formed in the course of reductive cleavage of oxygen and substrate oxidation to give NAD(P)H.

The present invention allows for the first time the enzyme-independent, indirect electrochemical regeneration of NADH or NADPH within the scope of oxygen-consuming, for example monooxygenase-catalyzed, reactions. Owing to the indirect electrochemical cofactor regeneration, a continuous substrate conversion is possible.

"Indirect" electrochemical regeneration of NAD(P)H in accordance with the present invention is given, if the cofactor is regenerated via a suitable redox catalyst which transfers the electrons required for the reduction from the cathode to the oxidized cofactor.

In a first aspect, the invention relates to an electroenzymatic method for preparing 2,3-dihydroxyphenyl derivatives of the formula I (I)

where R is unsubstituted phenyl or phenyl mono- or polysubstituted by, for example, halogen, such as F, Cl, Br or I, by CN or OH, in particular OH; is $C_1$–$C_6$-alkyl, for example methyl, ethyl, n-propyl or isopropyl, n-butyl, isobutyl or tert-butyl, and also n-pentyl or n-hexyl and, in each case, the branched analogs thereof; is halogen, for example F, Cl, Br or I; or is CN; and R' is H or OH, R' being in m position or p position, preferably p position to the 2-hydroxyl group of the phenyl ring, and where a) a monohydroxyphenyl compound of the formula II (II)

where R and R' have the abovementioned meanings, is converted using 2-hydroxybiphenyl 3-monooxygenase (HbpA) (E.C.1.14.13.44) in the presence of NADH and oxygen; and b) the $NAD^+$ formed is reduced electrochemically to NADH.

Preferably the electrochemical $NAD^+$ reduction is carried out in the presence of a hydridorhodium redox catalyst which can be prepared cathodically and can be regenerated. In this context, the redox catalyst is a preferably soluble rhodium complex which can be converted electrochemically into the hydridorhodium complex at a cathode potential in the range from –650 to –800 mV, measured against Ag/AgCl (saturated) (pH=6–9; T=20–60° C., in particular about 20 to 35° C., for example about 30° C.).

To carry out the HbpA-catalyzed reaction, particular preference is given to a rhodium complex of the formula III

[Cp Rh (III)(bpy)Cl]Cl    (III)

where

Cp is cyclopentadienyl or pentamethylcyclopentadienyl and bpy is 2,2'-bipyridyl, each of the pyridyl rings being unsubstituted or mono- or polysubstituted, in particular monosubstituted, by a donor group, the donor group being selected from methyl, methoxy and acetamido. Preferably, each of the pyridyl rings can have one of said substituents in 4 position or 5 position. In particular, the pyridyl rings having identical donor groups are substituted.

Within the scope of the inventive method with the participation of HbpA catalysis, the rhodium complex of the formula III is cathodically reduced to a hydridorhodium complex of the formula IIIa

[Cp Rh (I)(bpy)H]Cl with H as proton or

[Cp Rh (III)(bpy)H]Cl with H as hydride ion    (IIIa)

where Cp and bpy have the meanings mentioned above for formula III, and said hydridorhodium complex is then capable of $NAD^+$ reduction.

The inventive preparation of the dihydroxy compounds of the formula I is preferably carried out under the following conditions:

a) substrate concentration: (compound of the formula II): 0.01 to 50 mM, in particular 0.1 to 4 mM;

b) $NAD^+$ concentration: 0.01 to 5 mM, in particular 0.01 to 0.5 mM;

c) rhodium complex concentration: 1 $\mu$M to 5 mM, in particular 5 $\mu$M to 0.5 mM;

d) HbpA concentration: 1 to 5 000 U/l, in particular 10 to 1 000 U/l;

e) FAD concentration: 0 to 200 $\mu$M, in particular 0 to 20 or 1 to 20 $\mu$M;

f) catalase concentration: 0 to $1 \times 10^7$ U/l;

g) pH: 4 to 9, in particular 6 to 7.5 h) temperature: 10 to 40° C., in particular 20 to 35° C. or about 30° C.

i) cathode potential: –600 to –900 mV, in particular –650 to –800 mV j) oxygen input: 20 to 120 $cm^3$/(min·1), by blowing-in or in particular bubble-free via oxygen-permeable membranes or tubing, as described in [11], for example.

Electrode systems which are useful according to the invention are described in [12] and [13], for example. Representative, non-limiting examples of suitable cathode/anode pairs are: carbon cathode/platinum anode, such as in particular cylindrical carbon cathode (carbon felt, Sigraflex®)/platinum wire anode.

The substrates of the formula II converted according to the invention are generally accessible compounds and can be either purchased or prepared using common methods in organic chemistry. Nonlimiting examples which may be mentioned are:

2-hydroxy-$C_1$–$C_6$-alkylbenzenes, 2-hydroxyhalobenzenes, 2-hydroxybenzonitrile, and the 2,5-dihydroxy analogs of said benzene derivatives; 2-hydroxybiphenyl and polyhydroxylated biphenyls, for example 2,4-, 2,5- or 2,6-dihydroxybiphenyl; 2,n'-dihydroxybiphenyls (n'=2, 3 or 4); or 2,n',m'-trihydroxybiphenyls (n' and m' being different from one another and, in each case, being 2, 3 or 4).

The redox catalysts Used according to the invention are preferably [CpRh(bpy)Cl]Cl complexes. The preparation of said complexes is generally known and is carried out as described in [14] or [15]. The hydridorhodium complexes formed therefrom after electrochemical reduction at –700 mV (vs. Ag/AgCl$_{sat.}$), or else chemically with formate, convert $NAD(P)^+$ rapidly and quantitatively into the enzyme-active 1,4-NAD(P)H form [2,6].

A representative example which may be mentioned of usable enzymes is, representing the class of flavin-dependent monooxygenases, 2-hydroxybiphenyl 3-monooxygenase (HbpA, E.C. 1.14.13.44) from *P. azelaica*, which requires NADH as cofactor [7]. The enzyme is a homotetramer having a total mass of 256 kDa and catalyzes the selective ortho-hydroxylation of a number of α-substituted phenol derivatives. It is not possible to carry out said reaction chemically with comparable selectivity.

Diagram 1: Principle of the HbpA Reaction

The HbpA-catalyzed reaction is preferably carried out in an aqueous reaction medium, whose pH has been adjusted to a suitable value with common buffer substances not adversely affecting the conversion and the electrochemical process, for example HEPES, PIPES and in particular potassium phosphate buffer and Tris/HCl buffer. The buffer concentration is in the range from 20 mM to 0.2 M, in particular about 20 to 50 mM. The pH was adjusted to preferably from about 6 to 8, in particular about 7.5.

The reaction medium may contain further common additives, such as, for example, solubilizers for the substrate, cofactors, for example FAD or FMN, for the enzyme used, and the like.

For oxidation-sensitive enzyme systems, the use of antioxidants is sensible, where appropriate. If, for example, the method leads to the formation of hydrogen peroxide, which can adversely affect the enzyme activity, then the reaction may be carried out in the presence of catalase, added at a concentration of $1 \cdot 10^5$ U/l, for example.

The invention further relates to a method for electrochemical NAD(P)H regeneration, which can be used in an NAD(P)H-consuming oxidative enzymatic conversion of a substrate and in which an NAD(P)H-consuming oxidative enzymatic conversion of an oxidizable substrate is carried out in the presence of NAD(P)H and preferably with oxygen consumption and the NAD(P)$^+$ formed in the course of substrate oxidation is electrochemically reduced to give NAD(P)H. Said method is preferably suited to be carried out within the scope of monooxygenase-catalyzed reactions. In this connection, an NAD(P)H-dependent monooxygenase (from the class E.C. 1.14.-.-) is incubated with the oxidizable substrate in the presence of NAD(P)H and oxygen, and the NAD(P)$^+$ formed in the course of the reductive cleavage of oxygen and substrate oxidation is electrochemically reduced to give NAD(P)H.

According to a preferred variant of the invention, the electrochemical NAD(P)$^+$ reduction is carried out in the presence of a preferably soluble hydridorhodium redox catalyst which can be produced cathodically and can be regenerated.

The redox catalyst used in the inventive method for NAD(P)H-regeneration is preferably a rhodium catalyst which can be converted electrochemically into the hydridorhodium complex at a cathode potential in the range from −650 to −800 mV, measured against Ag/AgCl(saturated) (pH=6–9; T=20–60° C., in particular about 20 to 35° C., for example about 30° C.).

In the inventive method for NAD(P)H regeneration preferably rhodium complexes of the formula III'

[Cp Rh (III)(bpy)Cl]Cl    (III')

may be used, where

Cp is cyclopentadienyl or pentamethylcyclopentadienyl and bpy is 2,2'-bipyridyl, each of the pyridyl rings being unsubstituted or mono- or polysubstituted, in particular monosubstituted, by a donor group, the donor group being selected from methyl, methoxy and acetamido. Furthermore, the donor group contained may be a radical derived from polyethylene glycol for example from PEG 2 000 to 20 000. Preferably, each of the pyridyl rings can have one of said substituents in 4 position or 5 position. In particular, the pyridyl rings having identical donor groups are substituted.

The rhodium complex of the formula III' is cathodically reduced to a hydridorhodium complex of the formula IIIa'

[Cp Rh (I)(bpy)H]Cl with H as proton or

[Cp Rh (III)(bpy)H]Cl with H as hydride ion    (IIIa')

where Cp and bpy have the meanings mentioned above for formula III' and said hydridorhodium complex is then capable of NAD$^+$ reduction.

The inventive method for NAD(P)H regeneration is preferably carried out under the following experimental conditions:
a) NAD(P)+ concentration: 0.01 to 5 mM, in particular 0.01 to 0.5 mM;
b) rhodium complex concentration: 1 μM to 5 mM, in particular 5 μM to 0.5 mM;
c) monooxygenase concentration: 1 to 5 000 U/l, in particular 10 to 1 000 U/l;
d) cofactor concentration (such as, for example FAD): 0 to 200 μM;, in particular 0 to 20 or 1 to 20 μM;
e) catalase concentration: 0 to $1 \cdot 10^7$ U/l;
f) pH: 4 to 9, in particular 6 to 7.5
g) temperature: 10 to 40° C., in particular 20 to 35° C. or about 30° C.;
h) cathode potential: −600 to −900 mV, in particular −650 to −800 mV
i) oxygen input: 20 to 120 cm$^3$/(min·l) by blowing-in or in particular bubble-free via oxygen-permeable membranes or tubing, as described in [11], for example.

The substrates converted according to the invention are generally accessible compounds and can be either purchased or prepared using common methods in organic chemistry.

The redox catalysts used according to the invention are preferably [CpRh(bpy)Cl]Cl complexes. The preparation of said complexes is generally known and is carried out as described in [14] or [15]. The hydridorhodium complexes formed therefrom after electrochemical reduction at −700 mV (vs. Ag/AgCl$_{sat}$.), or else chemically with formate, convert NAD(P)$^+$ rapidly and quantitatively into the enzyme-active 1,4-NAD(P)H form [2,6].

The reaction is preferably carried out in an aqueous reaction medium, whose pH has been adjusted with common buffer substances not adversely affecting the conversion and the electrochemical process, for example HEPES, PIPES and in particular potassium phosphate buffer and Tris/HCl buffer. The buffer concentration is in the range from about 20 mM to 0.2 M, in particular about 20 to 50 mM. The pH was adjusted to preferably from about 6 to 8, in particular about 7.5.

The reaction medium may contain further common additives, such as, for example, solubilizers for the substrate, cofactors, for example FAD or FMN, for the enzyme used, and the like.

For oxidation-sensitive enzyme systems, the use of antioxidants is sensible. If, for example, the method leads to the formation of hydrogen peroxide, which can adversely affect the enzyme activity, then the reaction may be carried out in the presence of catalase, added at a concentration of $1 \cdot 10^5$ U/l, for example.

The inventive method for NAD(P)H regeneration can preferably be used for the following reaction types comprising an oxidative enzymatic conversion:
a) oxidation of saturated or unsaturated aliphatic or aromatic carbon atoms, in particular by hydroxylation, epoxidation and Baeyer-Villiger oxidation;
b) sulfur or selenium oxidation;
c) nitrogen oxidation or phosphorus oxidation;
d) oxidation of halides.

Nonlimiting examples of reaction type a):
(1) Hydroxylation on Aliphatic Carbon:

for example described in JP 75/54957 (Takeda)
(2) ω-Hydroxylation of long-chained fatty acids, catalyzed by cytochrome P450 monooxygenase; described, for example, in DE-A-199 35 115.5 (BASF AG)
(3) Hydroxylation of Allylic or Benzylic Carbons.

H. Fretz, W. D. Woggon, R. Voges *Hel. Chim. Acta*, 1989., 72, 391–400

H. L. Holland, T. S. Manoharan, F. Schweizer *Tetrahedron: Asymmetry*, 1991, 2, 335–338
(4) Epoxidation:

S. W. May, B. J. Abbot *J. Biol. Chem*, 1973, 248, 1725–1730
(5) Baeyer-Villiger Oxidation:

Roberts et al. *J. Mol. Cal. B Enzymatic*, 1998, 4, 111 ff
(6) Oxidation of Heteroaromatics:

in each case catalyzed by cyclohexanone monooxygenase; described by Walsh, C. T., et al., Angew. Chem., 1988, 100, 242; and Roberts, et al., J. Mol. Cat. B Enzymatic, 1998, 4, 111.

The invention also relates to the use of a redox catalyst according to the above definition for the continuous or discontinuous electrochemical regeneration of NAD(P)H, preferably in oxygen-consuming oxidation reactions, in particular in monooxygenase-catalyzed oxidation reactions, in particular oxidation reactions of the type described above.

Finally, the present invention relates to bioreactors for continuously or discontinuously carrying out oxygen-consuming, in particular monooxygenase-catalyzed electroenzymatic reactions, comprising in a reaction chamber a pair of electrodes and a mono- or biphasic liquid reaction medium comprising enzyme, in particular monooxygenase, substrate, NAD(P)H cofactor and a redox catalyst as defined above, with an electrode potential, which is suitable for transferring redox equivalents (electrons) to the redox catalyst, being present at the cathode.

Examples of suitable types of bioreactors are described in [16] and [17], which are hereby incorporated by reference.

The skilled worker may adjust operation of the reactor and process control to the particular requirements of the desired redox reaction. Mono- or biphasic reaction media may be used as may a compartmentation of the reaction chamber. Biphasic reaction systems are advantageous, for example, in the conversion of the substrates and/or formation of products which are only poorly soluble, if at all, in the aqueous reaction medium. It is, for example, possible to provide the substrate in the organic phase. Said substrate is continuously released into the aqueous phase, where it is converted, and the product formed is, where appropriate, released back to the organic phase. Compartmentation allows, for example, a separation in space and time of enzyme reaction and electrode reaction. Preference is also given to introducing the oxygen by passing in gas, in-particular by passing it in bubble-free, as described, for example, by Rissom in [4b], which is hereby incorporated by reference.

In the following the invention is illustrated in more detail with reference to the attached figures.

EXAMPLE 1

Electroenzymatic Oxidation of 2-Hydroxybiphenyl to 2,3-Dihydroxybiphenyl

Figure 1:
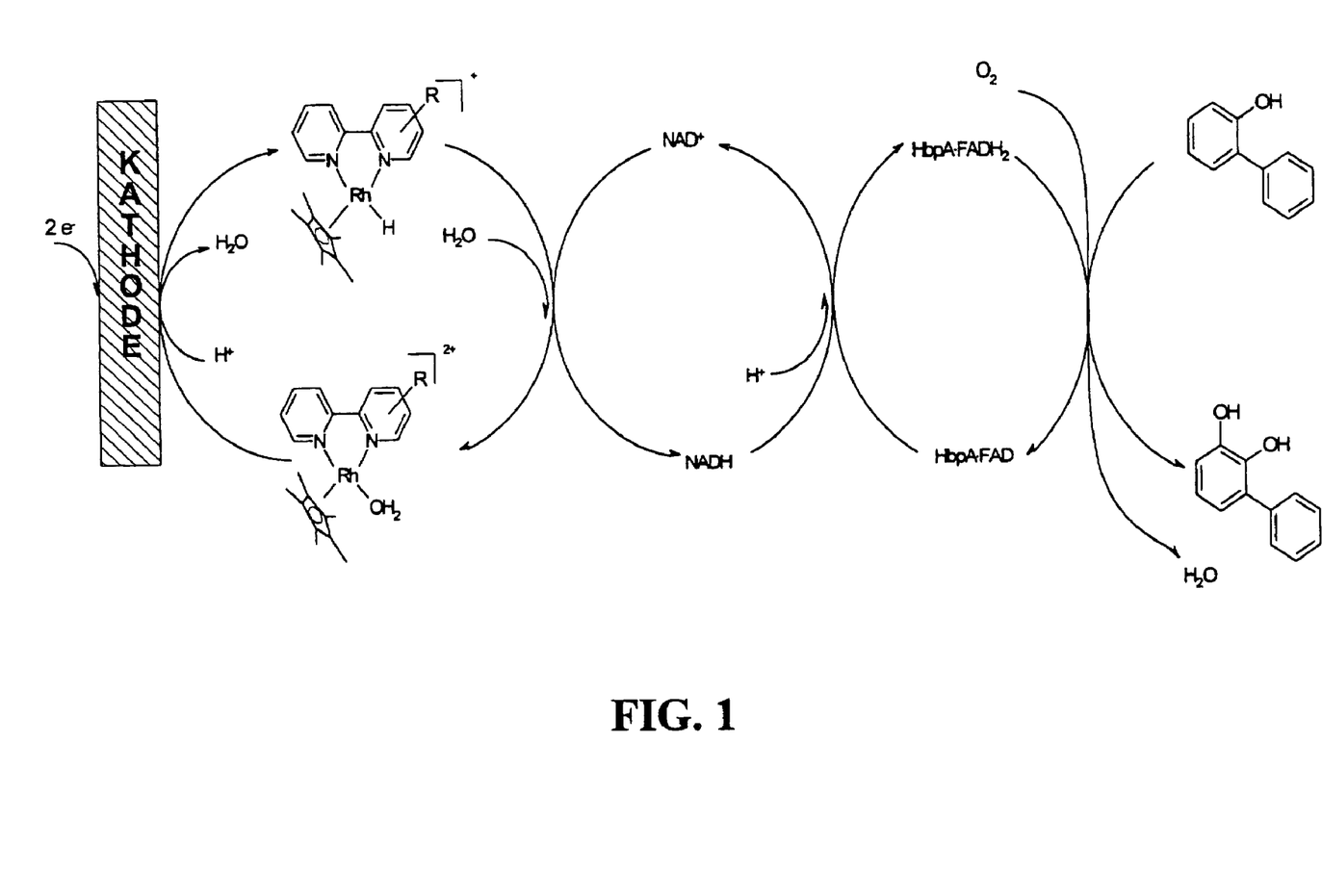
FIG. 1 shows a diagrammatic representation of the inventive electroenzymatic process of 2,3-dihydroxybiphenyl formation with simultaneous electrochemical NADH regeneration; the hydridorhodium(III) redox catalyst is formed and regenerated at the cathode. After transferring the hydride ion to NAD$^+$ and formation of NADH, said NADH reduces the monooxygenase, for example the prosthetic FAD group of 2-hydroxybiphenyl 3-monooxygenase, to give the active FADH$_2$ function. Said reduced form of the enzyme then catalyzes oxygenation of the substrate, for example 2-hydroxybiphenyl to give 2,3-dihydroxybiphenyl, in the presence of oxygen.
Figure 6:
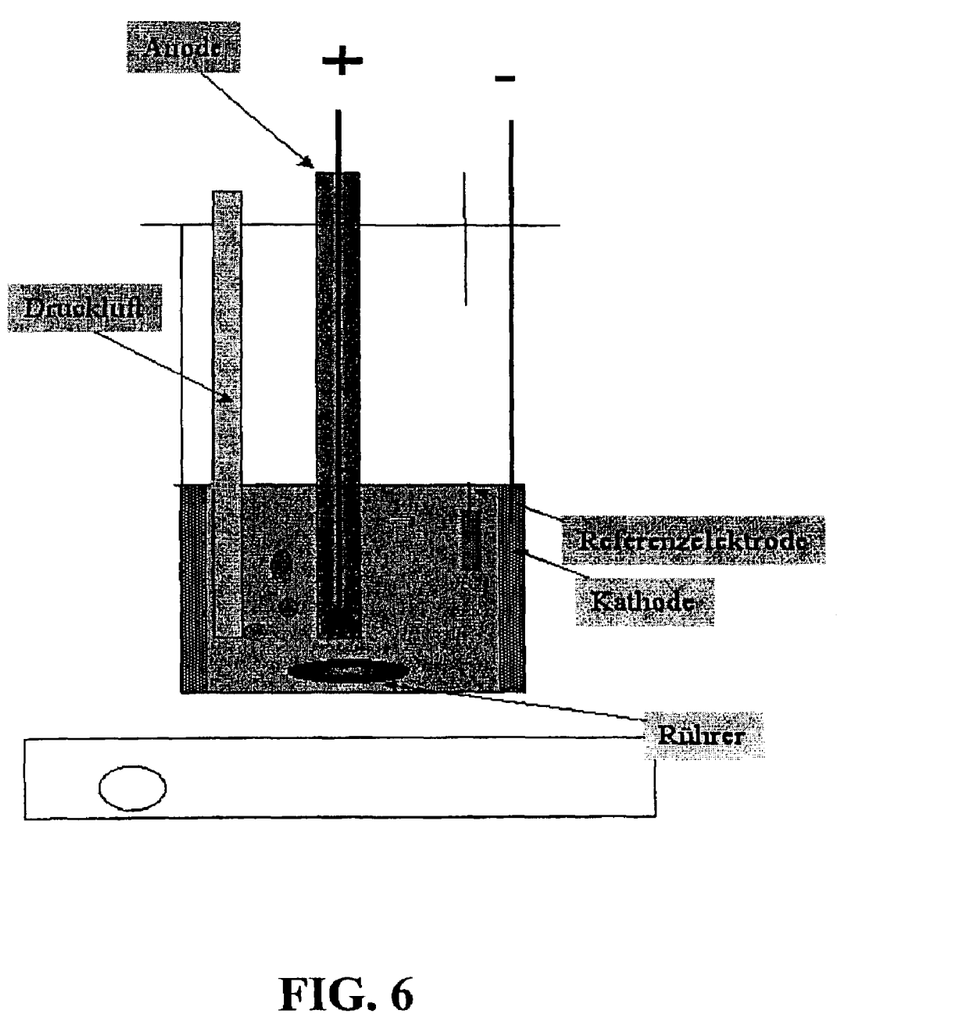
FIG. 6 shows in diagrammatic representation a suitable batch reactor comprising a reaction vessel with stirrer, ring cathode, central anode, reference electrode, feed of pressurized air into the reaction medium.

According to FIG. 1, the electroenzymatic conversion is carried out in a batch electrolysis cell, depicted diagrammatically in FIG. 6. The cathode used here is a cylindrical carbon felt electrode (approx. 27 cm$^3$ in volume). Sheathing of the platinum counterelectrode with a dialysis tubing (exclusion mass 10 kDa) achieves the conditions of a divided cell.

The cathode potential of −750 mV is adjusted against an Ag/AgCl$_{sat.}$ tube electrode. The oxidized cofactor NAD$^+$ (0.2 mM), [Cp*Rh(bpy)Cl]$^{2+}$ (0.1 mM), FAD (20 μM), catalase (250 000 U), HbpA (19 U) and the substrate (2 mM) are dissolved in 100 ml KP$_i$ buffer (50 mM, pH 7.5). The conversion is carried out at T=30° C. over a period of 5 hours.

The reaction progress is monitored by means of HPLC chromatography on an RP-18 column with methanol/water (0.1% H$_3$PO$_4$) 60:40 as eluent.

EXAMPLE 2

Effect of Dissolved Oxygen on NADH Regeneration

Figure 2:
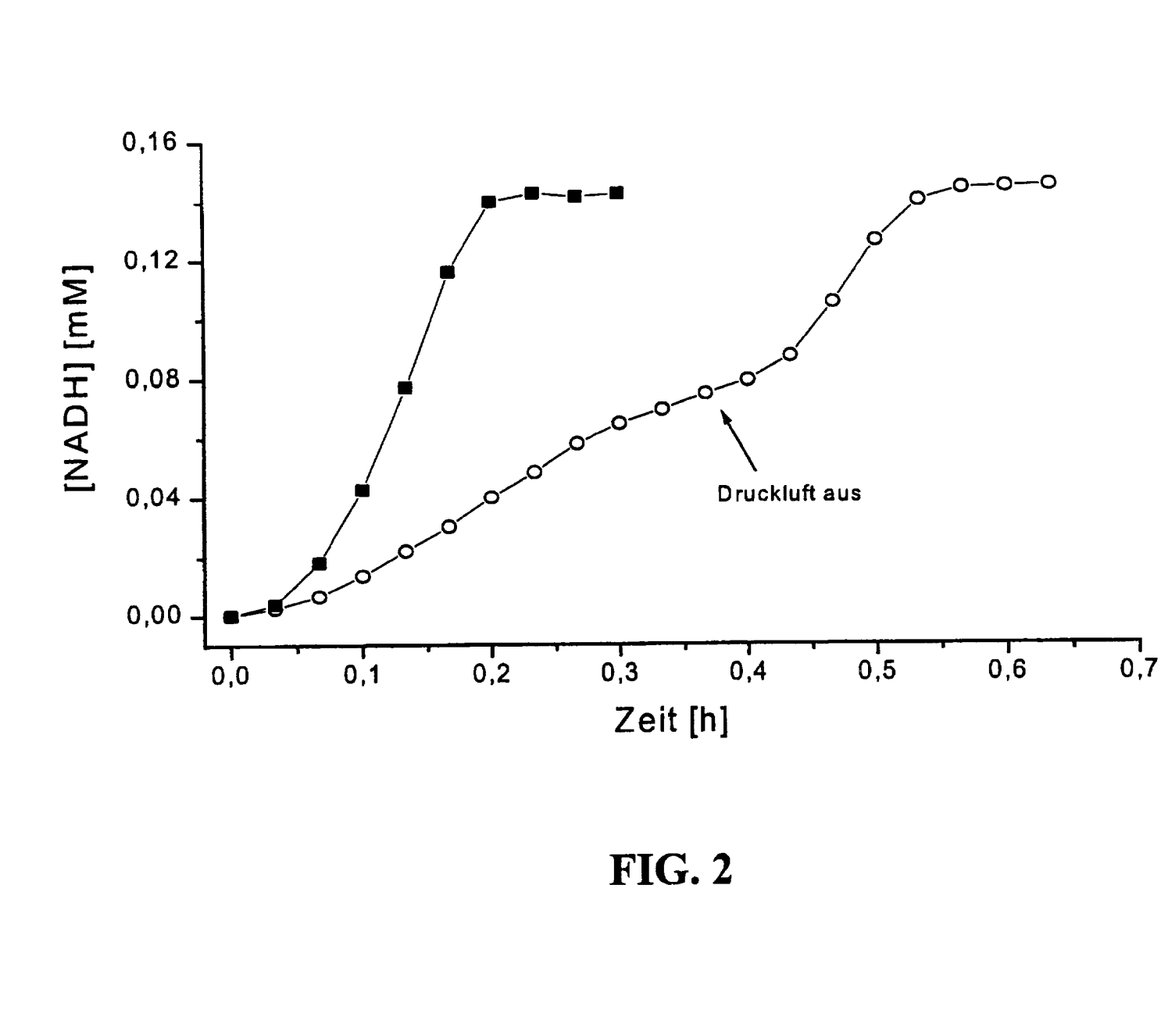
FIG. 2 shows the effect of O$_2$ on NADH formation with indirect electrochemical regeneration (■ without introduction of pressurized air; ○ with introduction of pressurized air at 10 cm$^3$/min FIG. 3 shows the postulated mechanism of the hydride oxidation FIG. 4 shows the effect of the oxygen content on the formation of 2,3-dihydroxybiphenyl with indirect electrochemical cofactor regeneration (○: no introduction of oxygen into the solution; ■: introduction of oxygen starting after 1 h).
Figure 3:
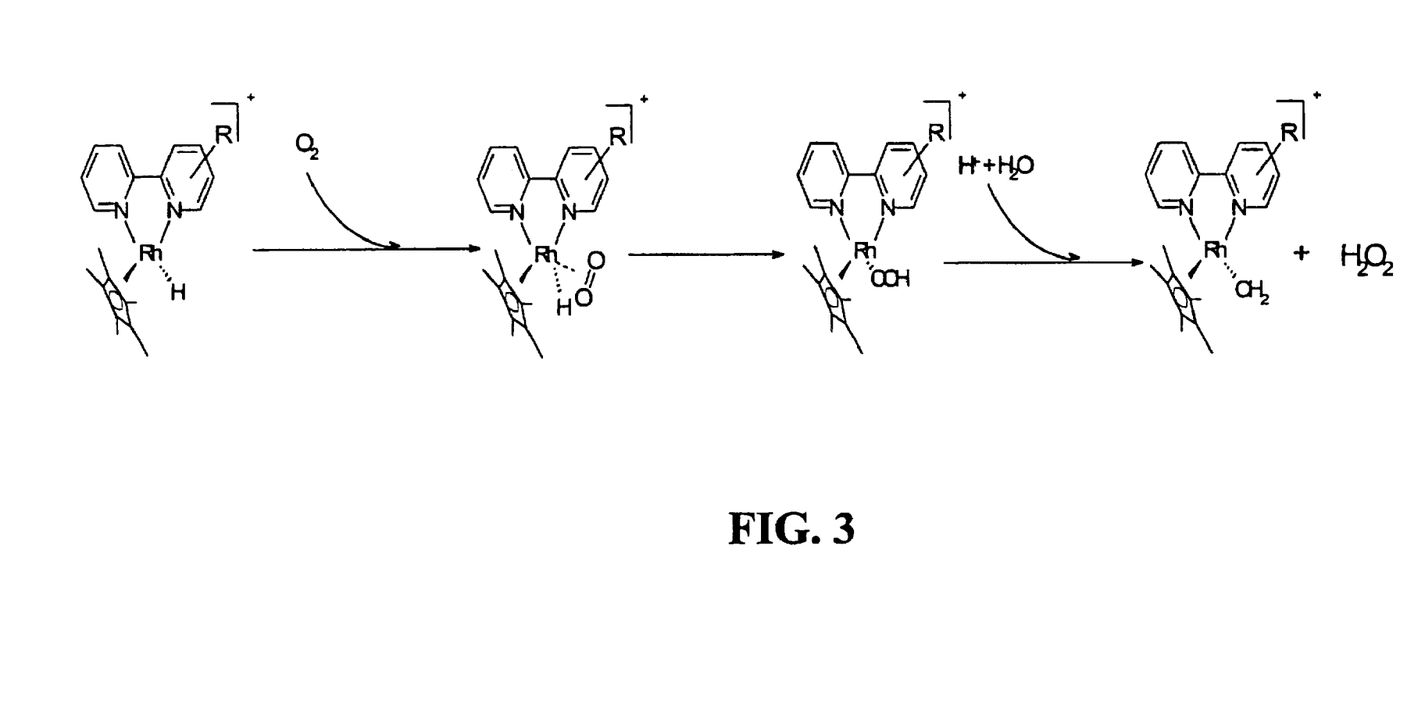

Since oxygen is part of the reaction sequence, the effect of dissolved oxygen on the components of the system has to be examined. This reveals that oxygen inhibits NADH generation both by the hydridorhodium complex formed chemically with formate and by the hydridorhodium complex formed electrochemically according to the invention (FIG. 2). As is evident from FIG. 2, an oxygen input of 10 cm$^3$/min, for example, reduces the rate of NADH formation from 1.1 mmol/l·h to 0.27 mmol/l·h. At an input of 15 cm$^3$/min, NADH formation is no longer detectable. However, the inhibition is reversible, since following interruption of the oxygen flow the rate of NADH formation nearly regains its optimum. Likewise, NADH concentration reaches its maximum. It was possible to detect hydrogen peroxide as a product of the reaction of the hydridorhodium complex with molecular oxygen, and a possible formation of hydrogen peroxide is indicated in FIG. 3. Moreover, at the applied potential hydrogen peroxide is also formed by direct reduction of the oxygen at the cathode. Therefore it is expedient to add catalase, since said catalase destroys hydrogen peroxide during the enzymatic conversion.

EXAMPLE 3

Effect of Oxygen Feed on the Conversion

Figure 4:
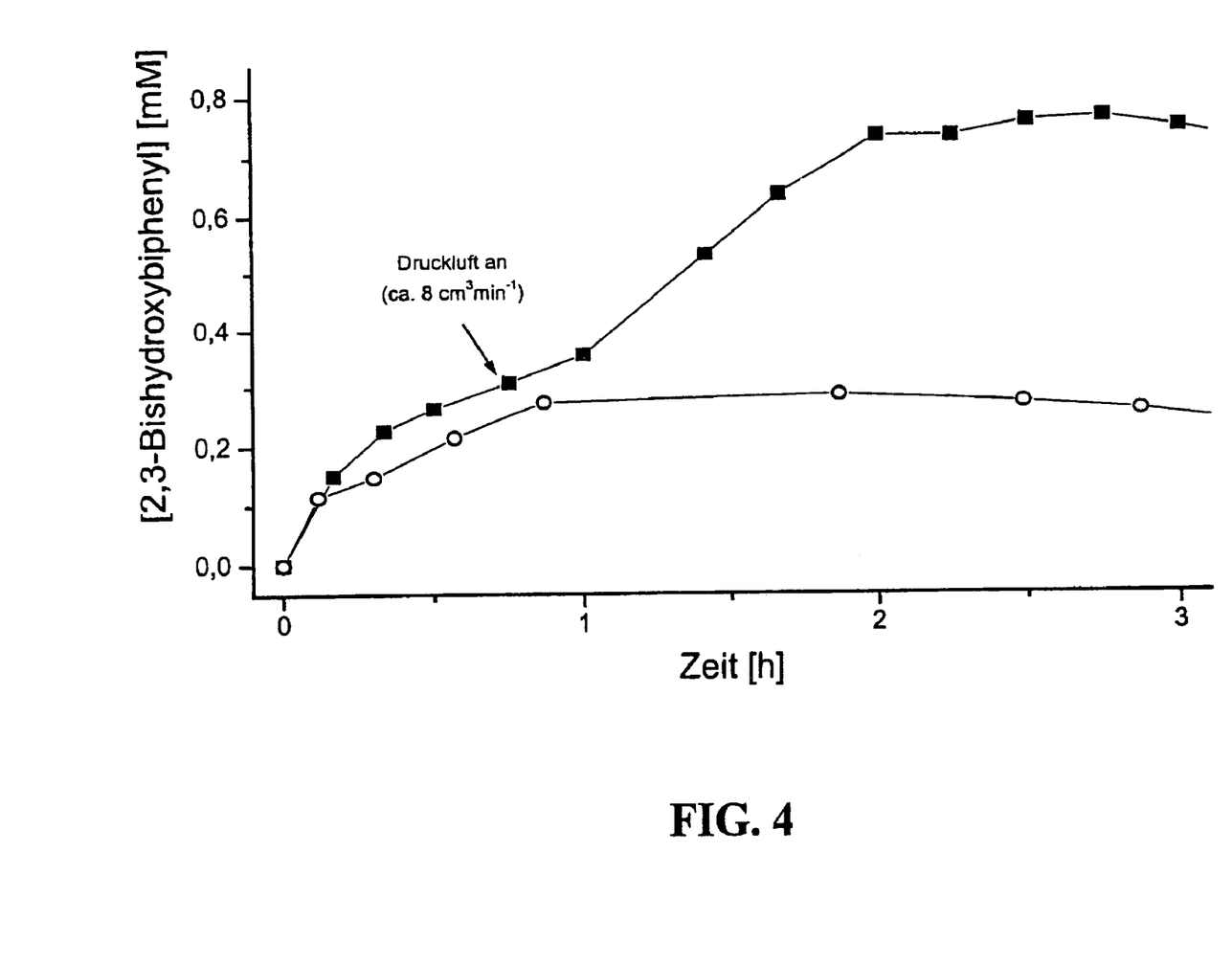
Figure 5:
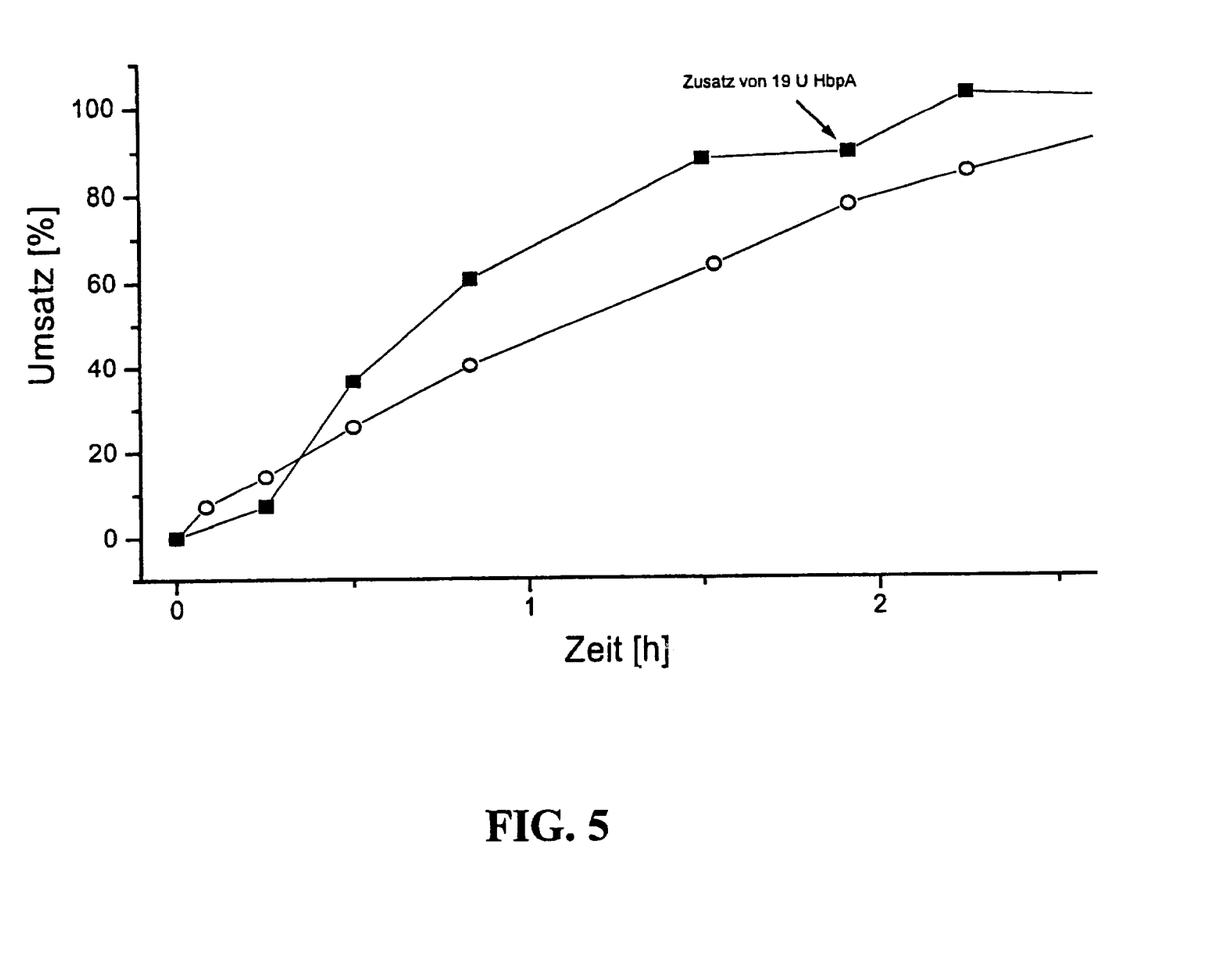
FIG. 5 shows a comparison of the conversion rates with chemical and indirect electrochemical hydridorhodium formation (○: redox-catalytic, chemical regeneration with formate as reducing agent; ■: indirect electrochemical regeneration).

The results in FIG. 4 show that in reactions without external oxygen feed, the conversion stagnates at approx. 20% after a short while (open circles and filled squares, respectively, up to approx. 1 h). With oxygen feed (8 cm$^3$/min) commencing after 1 h, conversion rate and thus product formation increase up to 1.1 mmol/l·h (202 mg/l·h). The turnover numbers produced by the mediator in this case are 11 h$^{-1}$. Similar values are achieved when generating the hydridorhodium complex chemically using sodium formate. FIG. 5 shows the conversion rates for the indirect electrochemical cofactor regeneration under the conditions mentioned, but with a continuous oxygen input of 10 cm$^3$/min, and for the redox-catalyzed process driven by formate (c(NaHCO$_2$)=160 mM; other conditions are the same). The productivity is approx. 50% of the already optimized fermentative or of the in vitro method with enzyme-coupled NADH regeneration (390 mg/l·h) [8].

The reaction rate is limited not by the formation of the hydridorhodium complex at the cathode but by competitive inhibition of the redox catalyst by the competing reaction with molecular oxygen (FIG. 4).

In the continuous electroenzymatic method of the invention, it should be readily possible to eliminate the negative effect of dissolved oxygen on the indirect electrochemical NADH regeneration by compartmentation of the whole system into individual modules. Following the electrochemical step in space and time, metering in of oxygen which is indispensible for the enzyme reaction minimizes the inhibitory effect of said oxygen on ADH regeneration.

Long term stability of the batch electrolyses carried out can be improved by reducing the denaturing action of non-bubble-free passing in of gas. This is because strong shear forces appear at the liquid/gaseous phase boundary and in the medium term lead to enzyme denaturation. Comparative experiments were able to show that HbpA still has more than 85% of its initial activity with thermostatting at 30° C. and stirring (250 min$^{-1}$), even after 12 h. With pressurized air feed commencing, said initial activity decreases, depending on the feed rate, by up to 70% within one hour. Using an enzyme-membrane reactor [9] can protect the producer enzyme from the adverse effect of the heterogenous oxygen input and consequently achieve long process run times. In particular, application of a biphasic reaction and of the resulting in situ metering in of the substrate and extraction of the catechol product should make an effective continuous process possible.

According to the invention it was for the first time possible to successfully carry out a conversion catalyzed by a flavin-dependent monooxygenase with indirect electrochemical NADH regeneration.

The present invention creates the basis for incorporating monooxygenases into organic syntheses both on the laboratory scale and for industrial use. Said class of oxidizing enzymes is of great interest for syntheses, since said enzymes are able, for example, to introduce hydroxyl functions into aromatic systems and also into nonactivated pure hydrocarbons. They can also transfer oxygen to heteroatoms or to double bonds with the formation of epoxides. Additionally, they catalyze Baeyer-Villiger oxidations. In all cases, enantiomerically pure products are accessible.

The underlying electrochemical NAD(P)H regeneration concept represents an effective and simply applicable alternative to previous in vivo methods or those methods which utilize an enzymatic regeneration system. It was possible to verify the general applicability, also under the conversion conditions of oxygen-dependent monooxygenases.

REFERENCES

[1] a) Hummel, W., et al., *Eur. J. Biochem.* 1989, 184, 1–13; b) Shaked, Z., et al., *J. Am. Chem. Soc.* 1980, 102, 7104–7108; c) Abril, O., et al., *Bioorg. Chem.* 1989, 17, 41–52; d) Seelbach, K., et al., *Tetrahedron Lett.* 1996, 37, 1377–1380
[2] a) Hilt, G., et al., *Liebigs Ann./Recueil* 1997, 2289–2296; b) Westerhausen, D., et al., *Angew. Chem.* 1992, 104, 1496–1498; Angew. Chem. Int. Ed. Engl. 1992, 31, 1529–1531 c) Ruppert, R., et al *Tetrahedron Lett.* 1987, 52(28), 6583–6586
[3] a) Walsh, C. T. *Acc. Chem. Res.* 1980, 13, 148–155; b) Walsh, C. T. et al., *Angew. Chem.* 1988, 100, 342–352; Angew. Chem. Int. Ed. Engl. 1988
[4] a) Hummel, W., et al.; *Appl. Microbiol Biotechnol.* 1986, 25, 175–185; b) Rissom, R., et al., *Tetrahedron Asymmetry* 1997, 15(8), 2523–2526
[5] Wong, C.-H., et al., *J. Am. Chem. Soc.* 1981, 103, 4890–4899

[6] a) Steckhan, E., et al., *Organometallics,* 1991, 10, 1568–1577; b) Ruppert, R., et al., *J. Chem. Soc., Chem. Commun.,* 1988, 1150–1151
[7] Suske, W. A., et al., *J. Biol. Chem.,* 1997, 272 (39), 24257–242565
[8] Held, M., et al., *Biotechnol. Bioeng.,* 1999, 62 (6), 641–648
[9] Wandrey, C., *Chem. Ing. Tech.* 1976, 48, 537
[10] Reipa, V., et al., *Proc. Natl. Acad. Sci.* USA, 1997, 94, 13554–13558
[11] Schneider et al., *Enzyme Microbiol. Technol.,* 1995, 17, 839
[12] Sawyer, D. T., Electrochemistry for Chemists, 2. Aufl, Wiley-Interscience; New York
[13] Kissinger, P. T., Laboratory Techniques in Electroanalytical Chemistry, Marcel Dekker, Inc.; New York/Basel
[14] Kölle, U., et al., *Angew. Chem.* 1987, 99, 572
[15] Kölle, U., et al., *Chem. Ber.* 1989, 122, 1869
[16] Kragl, U., et al., Chem. 1 ng. Tech., 1992, 499
[17] Brielbeck, B., et al., Biocatalysis, 1994, 10, 49

We claim:
1. An electroenzymatic method for preparing a 2,3-dihydroxyphenyl compound of the formula I where
R is unsubstituted, monosubstituted or polysubstituted phenyl, $C_1$–$C_6$ alkyl, halogen or CN; and
R' is H or OH; which comprises
a) converting a monohydroxyphenyl substrate compound of the formula II where R and R' have the abovementioned meanings, using 2hydroxybiphenyl 3-monooxygenase (HbpA) (E.C.1.14.13.44) in the presence of NADH and oxygen to obtain the compound of the formula I and NAD$^+$; and
b) reducing the NAD$^+$ formed to NADH electrochemically.
2. A method as claimed in claim 1, wherein the electrochemical NAD$^+$ reduction is carried out in the presence of a hydridorhodium redox catalyst which can be prepared cathodically and can be regenerated.
3. A method as claimed in claim 2, wherein the redox catalyst used is a rhodium complex which can be converted electrochemically into the hydridorhodium complex at a cathode potential in the range from –650 to –800 mV, measured against Ag/AgCl (saturated) (pH=6–9; T=20–30° C.).

4. A method as claimed in claim 3, wherein a rhodium complex of the formula III

[Cp Rh (III)(bpy)Cl]Cl    (III)

is employed, where
Cp is cyclopentadienyl or pentamethylcyclopentadienyl and
bpy is 2,2'-bipyridyl, each of the pyridyl rings being unsubstituted or mono- or polysubstituted by a donor group.

5. A method as claimed in claim 4, wherein the rhodium complex of the formula III is cathodically reduced to give a hydridorhodium complex of the formula IIIa

[Cp Rh (I)(bpy)H]Cl    (IIIa), which is capable of reducing $NAD^+$.

6. A method as claimed in claim 1, which is carried out under the following conditions:
a) substrate concentration: 0.1 to 4 mM;
b) $NAD^+$ concentration: 0.01 to 0.5 mM;
c) rhodium complex concentration: 5 μM to 0.5 mm;
d) HbpA concentration: 10 to 1 000 U/l;
e) FAD concentration: 0 to 200 μM;
f) catalase concentration: 0 to $1·10^7$ U/l;
g) pH: 6 to 7.5
h) temperature: 20 to 30° C.
i) cathode potential: −650 to −800 mV
j) oxygen input: 20 to 120 cm³/(min·l).

7. A method for electrochemical NAD(P)H regeneration from enzymatically formed $NAD(P)^{30}$, wherein
an NAD(P)H-consuming oxidative enzymatic conversion of an oxidizable substrate is carried out in the presence of NAD(P)H, and the $NAD(P)^+$ formed in the course of oxidation of the substrate is electrochemically reduced to NAD(P)H, and
wherein for performing the enzymatic reaction an NAD(P)H-dependent monooxygenase (of class E.C. 1.14.) is incubated with the oxidizable substrate in the presence of NAD(P)H and in the presence of oxygen, and the $NAD(P)^+$ formed in the course of the reductive cleavage of oxygen and oxidation of the substrate is electrochemically reduced to NAD(P)H, and
wherein the electrochemical $NAD(P)^+$ reduction is carried out in the presence of a hydridorhodium redox catalyst which can be prepared cathodically and can be regenerated.

8. A method as claimed in claim 7, wherein the redox catalyst used is a rhodium catalyst which can be converted electrochemically into the hydridorhodium complex at a cathode potential in the range from −650 to −800 mV, measured against Ag/AgCl (saturated) (pH=6–9; T=20–35° C.).

9. A method as claimed in claim 8, wherein a rhodium complex of the formula III

[Cp Rh (III)(bpy)Cl]Cl    (III)

is employed, where
Cp is cyclopentadienyl or pentamethylcyclopentadienyl and
bpy is 2,2'-bipyridyl, each of the pyridyl rings being unsubstituted or mono- or polysubstituted by a donor group.

10. A method as claimed in claim 9, wherein the rhodium complex of the formula III is cathodically reduced to give a hydridorhodium complex of the formula IIIa

[Cp Rh (I)(bpy)H]Cl    (IIIa)

which is capable of reducing $NAD^+$.

11. A method as claimed in any of claim 7, which is carried out under the following conditions:
a) $NAD(P)^+$ concentration: 10 μM to 0.5 mM;
b) rhodium complex concentration: 5 μM to 0.5 mM;
c) monooxygenase concentration: 10 to 1 000 U/l;
d) FAD concentration: 0 to 200 μM;
e) catalase concentration: 0 to $1·10^7$ U/l;
f) pH: 5 to 9
g) temperature: 20 to 35° C.
h) cathode potential: −650 to −800 mV
i) oxygen input: 20 to 120 cm³/(min·l).

12. A method as claimed in claim 7, wherein the oxidative enzymatic conversion comprises one of the following reaction types:
a) oxidation of saturated or unsaturated aliphatic or aromatic carbon atoms;
b) sulfur or selenium oxidation;
c) nitrogen oxidation or phosphorus oxidation;
d) oxidation of halides.

13. A bioreactor for carrying out in a continuous or discontinuous manner monooxygenase-catalyzed electroenzymatic reactions, which comprises in a reaction chamber a pair of electrodes and a liquid reaction medium comprising monooxygenase, substrate, NAD(P)H cofactor and a redox catalyst as defined in claim 2, with an electrode potential, which is suitable for transferring redox equivalents (electrons) to the redox catalyst, being present at the cathode.

14. A bioreactor as claimed in claim 13, wherein the liquid reaction medium is mono- or biphasic.

15. A method as claimed in claim 12, wherein the oxidation of saturated or unsaturated aliphatic or aromatic carbon atoms (a) comprises one of the following reaction types: a hydroxylation, an epoxidation or a Baeyer-Villiger oxidatior.

* * * * *

UNITED STATES PATENT AND TRADEMARK OFFICE
CERTIFICATE OF CORRECTION

PATENT NO. : 6,991,926 B2
APPLICATION NO. : 10/276227
DATED : January 31, 2006
INVENTOR(S) : Schmid et al.

It is certified that error appears in the above-identified patent and that said Letters Patent is hereby corrected as shown below:

Column 12,
Line 52, delete "using, 2hydroxybiphenyl 3-monooxygenase (HbpA)" and substitute -- using, 2-hydroxybiphonyl 3-monooxygenase (HbpA) --.
Line 67, delete "C.)." and substitute -- C). --.

Column 13,
Line 21, delete "c) rhodium complex concentration: 5 $\mu$M to 0.5 mm;" and substitute -- c) rhodium complex concentration: 5 $\mu$M to 0.5 mM; --.
Line 30, delete "from enzymatically formed NAD(P)$^{30}$, wherein" and substitute -- from enzymatically formed NAD(P)$^+$, wherein --.
Line 37, delete "(P)H-dependent monooxygenase (of class E.C. 1.14.) is" and substitute -- (P)H-dependent monooxygrenase (of class E.C. U4.-.-) is --.
Line 52, delete "C.)." and substitute -- C). --.

Signed and Sealed this

Twenty-seventh Day of June, 2006

JON W. DUDAS
*Director of the United States Patent and Trademark Office*